United States Patent

Ulrich et al.

[11] Patent Number: 5,571,190
[45] Date of Patent: Nov. 5, 1996

[54] IMPLANT FOR THE REPLACEMENT OF VERTEBRAE AND/OR STABILIZATION AND FIXING OF THE SPINAL COLUMN

[75] Inventors: Heinrich Ulrich, Galgenbergweg 28, D 89077 Ulm/Donau; Oleg J. P. Wolf, Berlin, both of Germany

[73] Assignee: Heinrich Ulrich, Ulm/Donau, Germany

[21] Appl. No.: 289,286

[22] Filed: Aug. 11, 1994

[30] Foreign Application Priority Data

Aug. 20, 1993 [DE] Germany ............... 43 28 062.5

[51] Int. Cl.⁶ ............... A61F 2/44; A61B 17/56
[52] U.S. Cl. ............... 623/17; 606/61
[58] Field of Search ............... 623/11, 16, 17, 623/18; 606/61, 60

[56] References Cited

U.S. PATENT DOCUMENTS 5,192,327  3/1993  Brantigan ............... 623/17
5,282,861  2/1994  Kaplan ............... 623/17

Primary Examiner—Debra S. Brittingham
Attorney, Agent, or Firm—Herbert Dubno

[57] ABSTRACT

An implant for spinal column resection stabilization or fixing has a pin with points lodged in vertebrae of the column and onto which an implant body composed of segments can be slid transversely so that a groove of the body receives the pin. The segments of the body are locked together with tooth crowns and can be rotated relatively to offset the mouths of the grooves.

20 Claims, 2 Drawing Sheets

IMPLANT FOR THE REPLACEMENT OF VERTEBRAE AND/OR STABILIZATION AND FIXING OF THE SPINAL COLUMN

FIELD OF THE INVENTION

Our present invention relates-to an implant for the replacement of vertebrae and/or for the stabilization and fixing of the spinal column, especially in conjunction with a spinal resection in which the implant is braced against upper and lower vertebrae. More particularly, the invention relates to an implant for these purposes having a centering pin at opposite ends of which points are provided for engaging in the vertebrae flanking the implant and between which the implant body is braced.

BACKGROUND OF THE INVENTION

Implants of this type (see Z. Orthop. 115 (1977) pages 118–122) have bracing pins or bars formed from two axially flush segments which are connected by a screw thread (a male threaded shank on one segment and a female thread or nut on the other segment) so that relative rotation of the two can displace the points further away from one another or toward one another depending upon the sense of rotation. Utilizing this pin-type implant, a large area bracing of the upper and lower portions of the resected spinal column relative to one another is not possible. The pin may not, therefore, satisfy the need for stabilization and fixing of the spinal column which may be especially important in a resection.

OBJECTS OF THE INVENTION

It is, therefore, the principal object of the present invention to provide an implant for the purposes described which has versatility for the replacement of a resected vertebra and also permits stabilization and fixing of the spinal column in the resection region.

Another object of this invention is to provide an implant for replacement of a vertebra and for stabilization and fixing of the spinal column in a resected region whereby drawbacks of earlier systems are avoided, and in particular, the device is easy to handle and of simple construction.

SUMMARY OF THE INVENTION

These objects and others which will become apparent hereinafter are attained, in accordance with the invention by providing upon the bracing pin, transverse to the pin axis, an implant body which has a laterally open groove enabling this body to be shoved onto the pin in the transverse direction, the body having end faces engageable with respective vertebrae in the resected region which brace against these vertebrae and can have surface structuring resisting slippage of the implant body relative to the vertebrae bodies against which the implant body is braced. The broad surfaces of the implant body and the countersurfaces of the vertebrae against which these end faces bear ensure a reliable fixing of the end faces of the implant body on the one hand and the vertebrae against which these end faces bear on the other.

More particularly a spinal implant for vertebral replacement, stabilization and fixation in a spinal column can comprise:

a bracing pin having centering points at opposite ends engageable in spaced apart vertebrae of the spinal column, and a pin shank between the points;

an implant body fitted laterally over the pin transversely to an axis thereof between the spaced apart vertebrae and having end surfaces abutting same, the body having a laterally open groove receiving the pin and extending between the end surfaces and opening at a mouth at a periphery of the body; and structuring on the surfaces for mutually fixing the surfaces and portions of the spaced apart vertebrae engaged thereby.

The pin which can be available in a series of standard-length pins selected to match the requirements, provide centering points which can be positioned with great accuracy and directly can be anchored in the vertebra bounding the resection region. Only then is the implant body slid over the bracing pin from the side so that the anchorages of the pin need not be altered and indeed are not even affected by the introduction of the implant body. The implant body which is positioned by the pin can bear with large surface areas against the vertebrae bounding the resectioned region, the seating of the surfaces against the vertebrae being secured by the surface structuring on the end faces of the implant body. The implant body is held by the pin against later movement.

According to a feature of the invention, the implant body is subdivided transversely to the pin into at least two adjoining body segments axially aligned along the pin and abutting one another at end faces of the body segments perpendicular to the axis, each of the body segments being formed with a segment of the groove having a respective segment of the mouth, the body segments being rotatable relative to one another to angularly offset the mouth segments about the axis, the end faces being formed with mutually engaging rings of teeth locking the body segments against angular self-displacement.

The subdivision of the implant body into at least two parts transversely to the pin so that the parts are aligned along the axis of the pin and have separating surfaces which are transverse to the axis to the pin and preferably perpendicular thereto, allows each of the two juxtaposed separating surfaces between the two parts to be formed with crowns of teeth centered on the axis and in engagement with one another to prevent relative angular displacement of the two parts at each pair of separating surfaces, once an angular position of the two parts has been set.

The two parts can thus be rotated relative to one another to adjust the positions and orientations of the end faces, one or both of which may be inclined to the axis of the pin. It will be apparent, moreover, that the relative rotation of the two parts can offset the mouths of the respective groove segments accommodating the centering pin. This effectively will prevent withdrawal of the implant body from the pin.

The implant body can thus be assembled from a number of parts on the support pin to satisfy any need in spinal column resection. The parts may be all of standard size and can be equipped with vertebrae-engaging end faces as well as the surfaces perpendicular to the axis and preferably provided with crowns of teeth, preferably radial teeth, for mutual engagement.

The relative angular displacement of two or more parts about the axis of the pin ensures that the pin can prevent lateral slip, especially slip in the radial direction in which the groove extends.

The teeth of the tooth crowns preferably also extend radially.

It is possible, moreover, to configure the surface structuring on the end faces of the body which are transverse to the axis and, where desired, perpendicular thereto, as planar surfaces provided with such radially-extending teeth in the form of a tooth crown. This latter configuration has the advantage that the segments of the implant body can have corresponding tooth crowns on both of their end faces and that the end faces of these segments can be interchangeably provided as the separating surfaces or as the end faces engageable with the adjacent vertebrae. Here a pair of teeth crowns interengage to prevent undesired relative angular displacement of the segments once they have been angularly offset to lock the implant body on the pin while other tooth crowns form the structuring for engaging vertebrae or other segments.

The end faces can be inclined to the axis of the pin and preferably these end faces can be provided upon body segments which have as the other end face, to form a separating surface, a face which is perpendicular to the axis of the pin.

In any case, an inclined end face of a segment should never be formed as a separating surface of the implant body since that would interfere with the desired relative rotation of the two parts about the axis of the pin.

The inclined end faces, moreover, need not be provided with tooth crowns and other surface structuring can be provided for them. For example, the end face can be provided with surface structuring in the form of an array of pins or projections projecting from the plane of the end face.

As a general matter, the pin can have a circularly cylindrical cross section with a diameter equal to the width of the groove. Advantageously the implant body segments or portions are also circularly cylindrical segments centered on the axis of the pin and having end faces which are parallel to one another and perpendicular to the pin or inclined thereto in the manner described. The body segments can be flush with one another.

When the implant body has one or more end faces which are inclined, preferably the inclination is such that the taper direction is in a direction which is perpendicular to the direction in which the groove extends radially from the center of the implant body toward the periphery. As a consequence, axially directed forces on the implant body will be transformed into forces which are transverse to the groove direction to minimize shifting of the parts or segments relative to the pin.

The implant body or its segments can be formed with throughgoing or blind bores forming part of the structuring described and as means to enable the groove of bone tissue into the implant body in situ. For similar reasons, the implant body or its segments can have a roughened surface to facilitate the growth of tissue into and onto the implant. In addition or alternatively, the implant body can be composed of a porous material, especially a porous metal foam.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
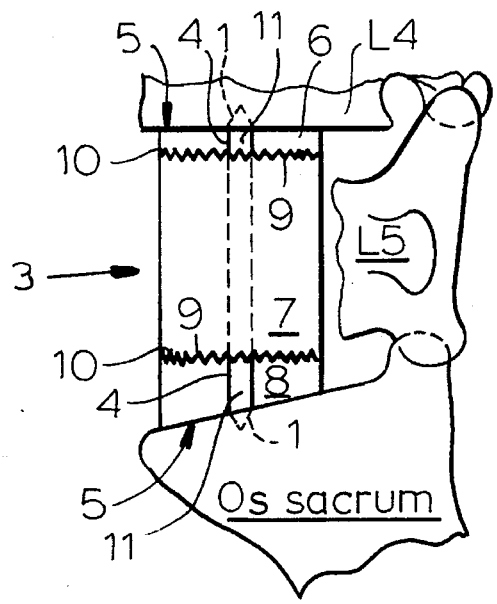
FIG. 1 is an elevational view of an implant according to the invention positioned in the spinal column between the lumbar vertebra L4 and the Os sacrum in highly diagrammatic form.
Figure 2:
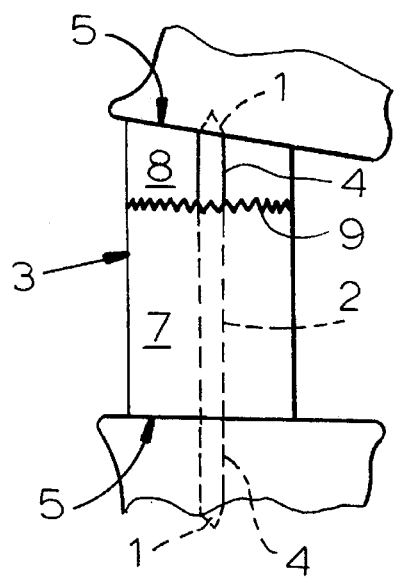
FIG. 2 is a view similar to FIG. 1 of a similarly positioned implant according to another embodiment of the invention.
Figure 3:
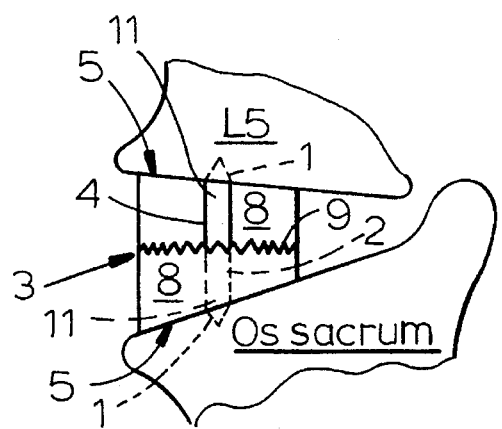
FIG. 3 is an elevational view of yet another embodiment of the implant in position between the fifth lumbar vertebra L5 and the Os sacrum.
Figure 4:
FIG. 4 is an elevational view of a pin for use with the implant bodies of the embodiments of FIGS. 1–3.

The implant shown in FIGS. 1 and 2 serves for replacement of a vertebra and for stabilization and fixing of the spinal column, e.g. in the case of a spinal resection. In FIG. 3 the implant serves exclusively to stabilize and fix the spinal column, being interposed between portions of the spinal column which normally adjoin one another rather than as a substitute for a resected vertebra.

The implant as a general matter comprises a support pin 2 having centering points 1 at its ends, the points being lodged in opposite portions of the spinal column, such as upper and lower vertebra flanking a resected region or upper and lower vertebrae to be supported by the implant.

The pin 2 penetrates with its points 1 into the vertebrae and is thus fixed in and relative thereto. On the pin 2 an implant body generally designated at 3 can be transversely fitted. For this purpose the implant body 3 is formed with a groove 4 laterally open along its periphery and dimensioned to accommodate the pin 2.

On its ends 5 engageable with the vertebrae, the implant body 3 is provided with structuring which enables the implant body to grip in the vertebrae. This structuring is described in greater detail below and serves on the one hand to fix the mutually-engaging surfaces of the implant body and the vertebra relative to one another and, of course, the surfaces of the two vertebrae flanking the implant body relative to one another.

The implant body 3 can be composed of a single piece between the two vertebrae or, preferably, as is shown in FIG. 1, can be subdivided into three body segments 6, 7, 8 or as shown in FIGS. 2 and 3 into two segments as represented at 7 and 8, respectively.

Figure 5:
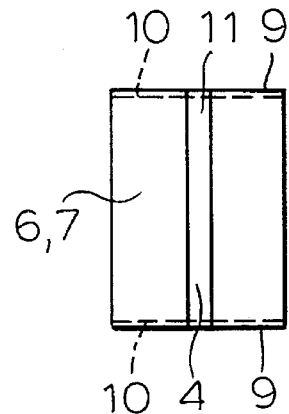
FIG. 5 is an elevational view of an implant body for use with this pin.

Segment 6 is a low height cylindrical segment with parallel end faces. Segment 7 is a taller cylindrical body with planar end faces (see also FIG. 5). Body segment 8 is a cylinder segment, one end of which has a surface inclined to the axis of the cylinder while the other end is perpendicular to the axis of the cylinder segment.

The segments when assembled lie against each other as planar separating surfaces 9 perpendicular to the axis of the pin 2.

Each of the separating surfaces 9 is formed with a tooth crown 10 centered on the axis of the pin 2 and having teeth which extend radially thereof. The interengagement of the tooth crowns 10 of the separating surfaces 9 prevents relative rotation of the segments 6, 7, 8 of each implant body 3 once the relative rotational positions have been established.

In mounting of the bodies 3, once the segments have been assembled on the pin 2 by transversely displacing the body onto the pin and with groove segments 4 thereof aligned, one or more of the segments may be rotated relative to the others to offset the mouths 11 of the respective grooves 4 angularly, thereby locking the body 3 formed by the segments 6, 7, 8 on the pin and such that the segments cannot shift relative to one another or to the pin 2. The grooves 4 of the parts 6, 7 and of the parts 7, 8, respectively, are each offset by 90° relative to the adjoining part. In FIG. 2, the grooves 4 of the parts 7, 8 and in FIG. 3 the two parts 8 are angularly offset by 180° relative to one another. In each case the median plane of the groove 4 of the part 8 is perpendicular to the plane of the drawing.

The tooth crowns 10 are formed with teeth which project from the planes of the separating surfaces 9 which extend radially as previously described. When the parts 6 and 7 have their parting surfaces 9 which are perpendicular to the axis of the pin 2 in engagement, these tooth crowns serve only to angularly fix the parts. A similar tooth crown can, however, also engage the vertebrae as the structuring described when, for example, one of the surfaces of the segment 7 bears directly against a vertebra.

The end faces 5 which are not provided with tooth crowns may be formed with projections or pins 12 forming the structuring. Tooth crowns 10 need not be provided on the inclined end faces 5 since these never will adjoin other inclined end faces or the portions of the segments provided with tooth crowns and adapted to form separating surfaces.

In all of the embodiments, the pin 2 is circularly cylindrical and has a diameter equal to the width of the groove 4. The pins 2 can be provided in standard lengths corresponding to the lengths required to project beyond the implant bodies as assembled from the several segments. The segments 6, 7, 8 moreover, may each be provided in a series of specified axial dimensions with the inclined surfaces having angles of inclination in various steps, etc. From the stock of these various implant body segments and pins, the requisite implant height and end face inclination for any given resection replacement can be provided.

Figure 6:
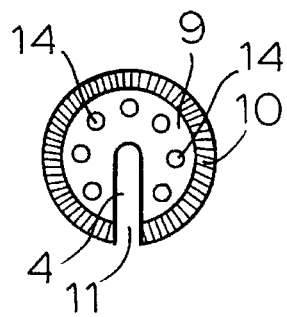
FIG. 6 is an axial end view of the implant body of FIG. 5.
Figure 7:
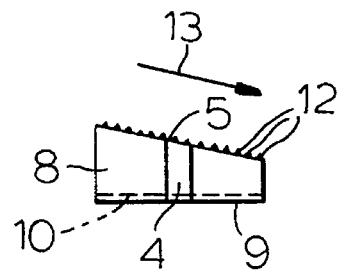
FIG. 7 is an elevational view of an implant body segment which can be used with the body of FIG. 5 or alone in accordance with the invention.
Figure 8:
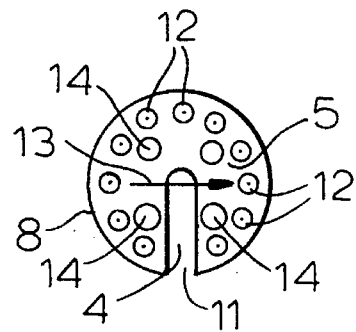
FIG. 8 is an axial end view of the body of FIG. 7.

The implant segments 6, 7 8 are also cylindrical bodies centered on the pin 2 flush with one another. As can be seen from FIGS. 5 and 6, the end faces of a cylindrical body may be parallel to one another or as shown in FIGS. 7 and 8 can be inclined to one another. When one of the surfaces is inclined, the taper direction represented by the arrow 13 can be perpendicular to the direction in which the groove 4 extends radially.

The implant body 3 can be formed with axially extending holes 4 which can be throughgoing or blind bores, especially short blind bores, to facilitate growth of tissue into the implant. The segments 6, 7, 8 can have roughened surfaces and/or can be composed of metal foam or sintered metal to permit growth and adhesion of tissue to the implant.

We claim:

1. Spinal implant for vertebral replacement, stabilization and fixation in a spinal column, said implant comprising:

a bracing pin having centering points at opposite ends engageable in spaced apart vertebrae of the spinal column, and a pin shank between said points;

an implant body fitted laterally over said pin in a direction transverse to an axis thereof between said spaced apart vertebrae and having end surfaces abutting same, said body having a laterally open groove receiving said pin and extending from end to end of said body between said end surfaces, opening at a mouth at an outer periphery of said body and extending into said body from said periphery to a center of said body; and structuring on said surfaces for mutually fixing said surfaces and portions of said spaced apart vertebrae engaged thereby.

2. The implant defined in claim 1 wherein said implant body is subdivided transversely to said pin into at least two adjoining body segments axially aligned along said pin and abutting one another at end faces of said body segments perpendicular to said axis, each of said body segments being formed with a segment of the groove having a respective segment of said mouth, said body segments being rotatable relative to one another to angularly offset said mouth segments about said axis, said end faces being formed with mutually engaging rings of teeth locking said body segments against angular self-displacement.

3. The implant defined in claim 2 wherein at least the teeth of one of said rings project from a respective one of said faces toward the other of said rings with radially extending flanks.

4. The implant defined in claim 2 wherein the structuring on at least one of said surfaces includes a ring of teeth engaging a respective one of said vertebrae.

5. The implant defined in claim 4 wherein said at least one of said surfaces is a planar surface perpendicular to said axis.

6. The implant defined in claim 2 wherein the structuring on at least one of said surfaces includes a multiplicity of sharp projections jutting from said one of said surfaces.

7. The implant defined in claim 2 wherein at least one of said surfaces is inclined to said axis.

8. The implant defined in claim 2 wherein said faces are inclined to said axis.

9. The implant defined in claim 2 wherein at least one of said surfaces is inclined to said axis, and said groove segment in the body segment formed with said one of said surfaces extends in a direction of fall of said one of said surfaces vertically and in a radial direction from a middle of the respective body segment to a periphery thereof.

10. The implant defined in claim 2 wherein at least one of said body segments has a roughened surface.

11. The implant defined in claim 10 wherein said one of said body segments is composed of a porous metal foam.

12. The implant defined in claim 2 wherein at least one of said surfaces is inclined to said axis, and said groove segment in the body segment formed with said one of said surfaces extends in a direction of fall of said one of said surfaces vertically and in a radial direction from a middle of the respective body segment to a periphery thereof.

13. The implant defined in claim 1 wherein said body is composed of a porous metal foam.

14. The implant defined in claim 2 wherein the structuring on at least one of said surfaces includes a multiplicity of sharp projections jutting from said one of said surfaces.

15. Spinal implant for vertebral replacement, stabilization and fixation in a spinal column, said implant comprising:

a bracing pin having centering points at opposite end engageable in spaced apart vertebrae of the spinal column, and a pin shank between said points;

an implant body fitted laterally over said pin transversely to an axis thereof between said spaced apart vertebrae and having end surfaces abutting same, said body having a laterally open groove receiving said pin and extending between said end surfaces and opening at a mouth at a periphery of said body and structuring on said surfaces for mutually fixing said surfaces and portions of said spaced apart vertebrae engaged thereby, said implant body being subdivided transversely to said pin into at least two adjoining body segments axially aligned along said pin and abutting one another at end faces of said body segments perpendicular to said axis, each of said body segments being formed with a segment of the groove having a respective segment of said mouth, said body segments being rotatable relative to one another to angularly offset said mouth segments about said axis, said end faces being formed with mutually engaging rings of teeth locking said body segments against angular self-displacement, said shank of said pin being of circular cross section with a diameter equal to a width of said groove.

16. The implant defined in claim 15 wherein at least the teeth of one of said rings project from a respective one of said faces toward the other of said rings with radially extending flanks.

17. The implant defined in claim 15 wherein the structuring on at least one of said surfaces includes a ring of teeth engaging a respective one of said vertebrae.

18. The implant defined in claim 17 wherein said at least one of said surfaces is a planar surface perpendicular to said axis.

19. The implant defined in claim 15 wherein at least one of said surfaces is inclined to said axis.

20. The implant defined in claim 15 wherein said faces are inclined to said axis.

* * * * *